United States Patent [19]

Karkhanis et al.

[11] 4,288,557
[45] Sep. 8, 1981

[54] ANTIGENIC COMPLEX FROM *N. GONORRHOEAE*

[75] Inventors: Yashwant D. Karkhanis, Fanwood; Dennis J. Carlo, South Amboy, both of N.J.

[73] Assignee: Merck & Co., Inc., Rahway, N.J.

[21] Appl. No.: 127,297

[22] Filed: Mar. 5, 1980

Related U.S. Application Data

[60] Division of Ser. No. 949,581, Oct. 12, 1978, Pat. No. 4,220,638, which is a continuation-in-part of Ser. No. 862,265, Dec. 20, 1977, abandoned.

[51] Int. Cl.³ .............................................. C07G 7/00
[52] U.S. Cl. .................................................... 435/272
[58] Field of Search .......................... 424/92; 435/272

[56] References Cited

U.S. PATENT DOCUMENTS 4,220,638  9/1980  Karkhanis et al. ................... 424/92

OTHER PUBLICATIONS

Thomas M. Buchanan and Robert J. Arko, The Journal of Infectious Disease, vol. 135, No. 6, pp. 879–887; 1977.
Kenneth H. Johnston et al., The Journal of Experimental Medicine, vol. 143, pp. 741–758; 1976.

*Primary Examiner*—Robert J. Warden
*Attorney, Agent, or Firm*—Gabriel Lopez; Theresa Y. Cheng; Hesna J. Pfeiffer

[57] ABSTRACT

An antigenic, immunogenic, non-toxic complex is obtained from the cell surface of *N. gonorrhoeae*.

5 Claims, No Drawings

ANTIGENIC COMPLEX FROM N. GONORRHOEAE

This is a division of Ser. No. 949,581, filed Oct. 12, 1978, now U.S. Pat. No. 4,220,638, which is a continuation-in-part of Ser. No. 862,265, filed Dec. 20, 1977, now abandoned.

BACKGROUND OF THE INVENTION

Although *Neisseria gonorrhoeae* was established as an etiological agent of gonorrhea over ninety years ago, knowledge of its cell surface antigenic structure is far from complete. Studies on the isolation of antigenic fractions from the cell surface of gonococcus have been numerous but work has been predominantly directed toward serological classification. Since these fractions were fragments of lipopolysaccharides and outer membrane proteins obtained under denaturing conditions, no general agreement on their identity could be reached among different investigators.

Even though gonorrohea is one of the most prevalent infectious diseases in many countries, information is still lacking concerning the nature of the immune response of the host. It has been well established that in certain human diseases of bacterial etiology, the protective immune response is directed primarily toward antigens that are found only in the virulent forms. Since morphological studies of gonococcus have shown that Type 1 and 2 are virulent forms (Kellog et al., 1963; Kellog et al., 1968), these types have become the subject of further investigations in attempts to isolate a prophylactic immunogen.

OBJECTS OF THE INVENTION

It is an object of the present invention to provide an antigenic, immunogenic, non-toxic complex from the cell surface of *N. gonorrhoeae*. Another object is to provide a complex which protects against *N. gonorrhoeae*. A further object is to provide a simple method for preparing this antigen. Yet another object is to provide compositions for the safe and effective administration to mammalian species of this antigen. Still another object is to provide a vaccine which protects against *N. gonorrhoeae*. These and other objects of the present invention will become apparent from the following description.

SUMMARY OF THE INVENTION

An antigenic, immunogenic, non-toxic complex is obtained from the cell surface of *N. gonorrhoeae* by extracting homogenized cells in the presence of a salt as a pH of from about 6.8 to about 8.3, removing cell solids, removing RNA and DNA, and isolating an active fraction having a molecular weight of about 9,000,000 consisting of several subunits ranging in molecular weight from 100,000 to 10,500.

DETAILED DESCRIPTION

The Melvin strain, Type 1, of *N. gonorrhoeae* used in this study was obtained from Mr. W. J. Brown at the Communicable Disease Center, Atlanta, Ga. An unrestricted deposit of this organism was made with the American Type Culture Collection on Dec. 13, 1977 under Accession No. 31356. The bacteria are grown in agar and cells from the agar are used to inoculate a fermentor. The cells are harvested at the stationary phase of growth and stored at $-20°$ C. if not used immediately.

The cell paste is homogenized in a salt solution at a pH of from about 6.8 to about 8.3 for a time insufficient to cause lysis. The resulting mixture is stirred, preferably at lowered temperature, typically from about $4°$ to about $8°$ C. for several hours, typically for from about 10 to about 15 hours. Any salt solution may be used as long as it is non-injurious to the cell surface of *N. gonorhoeae*. Examples of suitable salts are Tris-HCl, phosphate buffered saline, LiCl, and physiological saline, or LiCl. Tris-HCl is preferred.

The stirred mixture is then centrifuged to remove cellular debris. Typically the pellet is removed at from about 30,000 to about 50,000 xg for from about 15 minutes to about 1 hour. In general longer times are employed with lower g and shorter times are employed with higher g. The supernatant resulting from the centrifugation is then treated to remove RNA and DNA. This may be effected by enzymatic digestion e.g., RNase and DNase. The digested mixture is subjected to treatment effective to fractionate molecules based on their molecular weight. As examples of such treatments there may be mentioned gel filtration, ultrafiltration, high speed ultracentrifugation or density gradient separation. Gel filtration is a particularly suitable method for this fractionation. The antigenically active fraction from the molecular weight fractionation is the desired immunogenic, non-toxic complex of the present invention.

The antigenic complex has a molecular weight of from about 9,200,000 to about 9,500,000 consisting essentially of several subunits ranging in molecular weight from about 100,000 to about 10,500. There are 5 major bands present in approximately equal amounts of molecular weight about 68,000, about 50,000, about 34,000, about 27,000 and about 10,500. These five bands account for over 80% of the complex. On a dry weight basis the antigen contains from about 90 to about 95% protein (Lowry method using bovine serum albumin as a standard), not more than about 10%, lipopolysaccharide, and typically not more than about 5% (Perry et al., Can J. Biochem., 53, 623 (1975), about 2% carbohydrate and less than 1% of RNA, DNA and phospholipids. RNA and DNA are assayed by the procedure of Schneider, *Methods Enzymol.* 3, 680 (1957), and phospholipids by the procedure of *Ames Methods Enzymol.*, 8, 115 (1966).

The antigenic, immunogenic complex from the cell surface of *N. gonorrhoeae* may be sterilized by filtration or treatment by chemicals such as thimerosol, phenol, formaldehyde and the like, and subdivided into a suitable container for distribution and administration as a vaccine. It may be administered in a suitable physiologically acceptable medium such as, for example, water for injection, saline, phosphate buffered saline, and the like. It may be combined with adjuvants such as, for example, as disclosed in U.S. Pat. No. 3,983,228 issued Sept. 28, 1976 and carriers, e.g., alum.

The following examples illustrate the present invention without, however, limiting the same thereto.

EXAMPLE 1

A culture of *N. gonorrhoeae*, Melvin strain, ATCC 31356, is used to inoculate agar culture overnight. Cells growing on the agar culture are used to inoculate a 2 liter flask which is grown overnight and the contents used to inoculate a 14 liter fermentor which is grown overnight and the contents used to inoculate a 200 liter fermentor containing Frantz medium [J. Bact., 43, 757, (1942)]. The fermentation is conducted at a temperature of 37° C. and is stopped when the bacteria reach their stationary phase of growth. To the fermentation is added thimerosol at a concentration of 1:10,000. The cells are centrifuged in a Sharpless centrifuge and the cell paste is collected.

Approximately 30 g of cell paste are homogenized in 100 ml of Tris-HCl buffer in a Sorvall Omni-mixer for 1-2 minutes at a speed setting of 2. The mixture is transferred to a flask and the homogenization flask is washed with an additional 100 ml of Tris-HCl buffer. The mixture is stirred at 4° C. for 15 hours. After extraction, the material is centrifuged at 39,100 xg for 30 minutes in a Sorvall RC-2 centrifuge, and the residue is discarded. The supernatant is made 20 mM in $MgCl_2$ and treated with RNase and DNase (10 µg/ml) at 37° C. for 45 minutes. The digested material is applied to an Agarose A-1.5 m chromatography column and the fractions recovered from the column are tested for presence of antigenic material by the Ouchterlony immunodifusion assay technique using antibody obtained as described in Example 2. Fractions containing antigenic material are pooled and applied to a Sepharose 6B chromatography column. The column is eluted with 50 mM ammonium bicarbonate buffer, pH 8.5 and the fractions tested for presence of antigenic material as indicated above. The active fraction yields 100 mg of an antigenic, immunogenic non-toxic complex having a purity of from 90-95%.

EXAMPLE 2

Live cells of N. gonorrhoeae, Melvin strain, ATCC 31356 are inoculated intravenously into a group of 4 New Zealand white rabbits. The procedure consists of intravenous inoculation on days 1, 3, 10 and 14 and bleeding 7 days later. This is followed by a rest period of one month after which the animals receive 2 additional injections on days 3 and 7 with bleeding 9 days later. Sera with good antibody activity are obtained.

Antisera against the purified antigen preparation of Example 1 is prepared by intramuscular inoculation in a group of 3 rabbits. Initial inoculation consists of 50-100 µg of antigen emulsified in an equal volume of complete Freund's adjuvant. Subsequent booster doses of equal amounts of antigen are emulsified in an equal volume of incomplete Freund's adjuvant and administered intramuscularly. The booster doses are given every three weeks. Rabbits are routinely bled on the 7th and 14th day and receive a booster of antigen following the bleeding. Sera with good antibody activity are obtained following the second injection.

EXAMPLE 3

The antigenically active material of Example 1, 250 µg, is injected into a group of 10 CD-1 albino male mice weighing approximately 10 g. A second group of 10 mice serve as control. After one week the animals in each group are challenged with $10^7$ live cells of N. gonorrhoeae. Fifty replicates of the foregoing procedure are carried out. Ninety to one hundred percent of the animals in the control groups are found to die within 24 hours whereas 90-100% of the animals in the group receiving the antigenic material prior to challenge survive.

EXAMPLE 4

Saline, 20 ml, is added to 50 mg. of the complex obtained in Example 1 and the resulting suspension is sterile filtered through a 0.45µ micropore filter and asceptically filled into forty 0.1 ml vials. Each vial contains 0.25 mg of complex. The vials are stored at −20° C. until used.

EXAMPLE 5

A culture (10 grams, wet weight) of N. gonorrhoeae cells is suspended in 200 ml of 0.2 M LiCl. The cells are homogenized for about 1 minute at setting 2 of a Sorvall Omnimixer. The cells are extracted at 45° C. for 2 hours at 200 rpm in a gyratory shaker. The extract is centrifuged at 10,000 rpm (9,000 xg) and the supernatant aspirated. To the recovered supernatant, 580 ml, there is added 117.9 mg of $MgCl_2$ and 5.8 mg of DNase and 0.42 ml of RNase. The resulting mixture is stirred for 30 minutes at 37° C. in a gyratory water bath shaker at setting 3. The mixture is then dialyzed overnight with 2 changes of water. The dialyzed liquid is lyophilized to yield 769.72 mg of crude gonococcal extract. The lyophilized extract is dissolved in 770 ml of distilled water, stirred and centrifuged at 13,000 rpm for 30 minutes. The supernatant is then applied to an Agarose A-5 m column and the column eluted with 0.15 M NaCl. The material eluted from the column having an adsorption at 230 nm is pooled, dialyzed and lyophilized to yield the purified gonococcal complex.

Four groups of mice are vaccinated subcutaneously with 250 µg of the purified gonococcal antigen. A fifth group of unvaccinated mice serves as control. Eight days after vaccination, the mice are challenged with $1 \times 10^7$ live virulent N. gonorrhoeae cells. The percent of protection is determined by observation of the number of survivors after 48 hours. The following results are obtained:

| Group | No. in Group | No. Dead | % Protection |
| --- | --- | --- | --- |
| 1 | 10 | 0 | 100 |
| 2 | 10 | 0 | 100 |
| 3 | 7 | 1 | 90 |
| 4 | 10 | 2 | 80 |
| 5 (control) | 10 | 8 | 20 |

What is claimed is:

1. A method of obtaining an antigenic, immunogenic, complex obtained from the cell surface of N. gonorrhoeae which is protective against N. gonorrhoeae having a molecular weight of from about 9,200,000 to about 9,500,000, over 80% of the complex being formed of five sub-units in approximately equal amount having molecular weight of about 68,000, about 50,000, about 34,000, about 27,000 and about 10,500, the complex containing a dry weight basis from about 90 to about 95% protein, up to about 7% lipopolysaccharide, about 2% carbohydrate and less than 1% of RNA, DNA and phospholipids which comprises stirring a homogenized cell paste of N. gonorrhoeae for from about 10 to about 15 hours, removing cellular debris, RNA and DNA from the homogenized extract, and separating a fraction having a molecular weight in excess of about 9,000,000.

2. A method according to claim 1 wherein the cellular debris is removed by centrifugation.

3. A method according to claim 2 wherein the centrifugation is carried out at from about 30,000 xg to about 50,000 xg.

4. A method according to claim 2 wherein the RNA and DNA are removed by treatment with an enzyme.

5. A method according to claim 2 wherein the fraction is separated by gel filtration.

* * * * *